United States Patent
Riederer

(10) Patent No.: US 9,594,143 B2
(45) Date of Patent: Mar. 14, 2017

(54) SYSTEM AND METHOD FOR CONTROLLING CALIBRATION AND DELAY PHASES OF PARALLEL, CONTRAST-ENHANCED MAGNETIC RESONANCE IMAGING

(75) Inventor: Stephen J. Riederer, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1199 days.

(21) Appl. No.: 13/601,417

(22) Filed: Aug. 31, 2012

(65) Prior Publication Data

US 2013/0063146 A1    Mar. 14, 2013

Related U.S. Application Data

(60) Provisional application No. 61/532,487, filed on Sep. 8, 2011.

(51) Int. Cl.
| | | |
|---|---|---|
| A61B 5/00 | (2006.01) | |
| G01R 33/563 | (2006.01) | |
| A61B 5/05 | (2006.01) | |
| G01R 33/561 | (2006.01) | |

(52) U.S. Cl.
CPC ............ *G01R 33/5635* (2013.01); *A61B 5/05* (2013.01); *G01R 33/5611* (2013.01)

(58) Field of Classification Search
CPC .... G01R 33/5635; G01R 33/5611; A61B 5/05
See application file for complete search history.

(56) References Cited

U.S. PATENT DOCUMENTS

| | | | | | |
|---|---|---|---|---|---|
| 2006/0273792 | A1* | 12/2006 | Kholmovski | ...... | G01R 33/5611 324/309 |
| 2008/0024132 | A1* | 1/2008 | Brau | .................. | G01R 33/5611 324/309 |
| 2008/0187196 | A1* | 8/2008 | Hu | ...................... | G01R 33/5611 382/128 |

(Continued)

OTHER PUBLICATIONS

"Parallel Imaging in MRI: Technology, Applications, and Quality Control." AAPM Report No. 118: Jun. 2015.*

(Continued)

*Primary Examiner* — Amanda Lauritzen Moher
(74) *Attorney, Agent, or Firm* — Quarles & Brady LLP

(57) ABSTRACT

A system and method for performing parallel magnetic resonance angiography includes controlling operation of a magnetic gradient system and an RF system to perform a calibration data pulse sequence to begin acquiring calibration data for use in a parallel imaging reconstruction process after receiving an indication that the subject has received a dose of a contrast agent. The acquisition of the calibration data is discontinued before the contrast agent reaches a peak concentration within a region of interest (ROI) of the subject and operation of the magnetic gradient system and RF system is controlled to perform an imaging pulse sequence in accordance with a parallel imaging acquisition to begin acquiring image data from the ROI. The image data is reconstructed into an image of the ROI using the calibration data.

18 Claims, 8 Drawing Sheets

(56) References Cited

U.S. PATENT DOCUMENTS

2009/0238430 A1* 9/2009 Haider .................. G01R 33/482
382/131

OTHER PUBLICATIONS

Earls JP, et al., "Hepatic arterial-phase dynamic gadolinium-enhanced MR imaging: optimization with a test examination and a power injector" Radiology (1997) 202:268-273.

Wilman Ah, et al., "Fluoroscopically-triggered contrast-enhanced three-dimensional MR angiography with elliptical centric view order: application to the renal arteries" Radiology (1997) 205:137-146.

Wilman Ah, et al., "Performance of an elliptical centric view order for signal enhancement and motion artifact suppression in breath-hold three dimensional gradient echo imaging" Magn Reson Med (1997) 38:793-802.

Pruessmann KP, et al., "SENSE: sensitivity encoding for fast MRI" Magn Reson Med (1999) 42:952-962.

Weiger M, et al., "2D Sense for faster 3D MRI" Magma (2002) 14:10-19.

Griswold Ma, et al., "Generalized autocalibrating partially parallel acquisitions (GRAPPA)" Magn Reson Med (2002) 47:1202-1210.

* cited by examiner

SYSTEM AND METHOD FOR CONTROLLING CALIBRATION AND DELAY PHASES OF PARALLEL, CONTRAST-ENHANCED MAGNETIC RESONANCE IMAGING

CROSS-REFERENCE

This application is based on, claims priority to, and incorporates herein by reference in its entirety, U.S. Provisional Application Ser. No. 61/532,487, entitled, "Modified Calibration of SENSE-Accelerated Time-Resolved Contrast Enhanced MRA," and filed Sep. 8, 2011.

STATEMENT REGARDING FEDERALLY SPONSORED RESEARCH

This invention was made with government support under HL070620 awarded by the National Institutes of Health. The government has certain rights in the invention.

BACKGROUND OF THE INVENTION

The present invention relates generally to systems and methods for magnetic resonance imaging ("MRI") and, more particularly, the invention relates to systems and methods for image acquisition of contrast-enhanced magnetic resonance angiography images using parallel-imaging MRI techniques.

Contrast-enhanced magnetic resonance angiography ("CE-MRA") is a method whereby magnetic resonance imaging ("MRI") techniques are used to image blood vessels of the body after administering a contrast agent to the patient. Typically, a moderate amount of a gadolinium-based, or other type of, contrast agent is injected into a vein in the patient's arm. The contrast agent then makes its way into circulation through the patient's vasculature. The presence of the contrast agent in the blood causes the net relaxation time of the blood to be altered from its unenhanced value. MR acquisition methods can exploit this change in relaxation time, causing the enhanced blood within the vasculature to be significantly brighter compared to other structures within the imaging field-of-view ("FOV").

There are technical challenges associated with performing CE-MRA. First, to obtain a three-dimensional (3D) image with adequate spatial resolution, it is necessary to have a sufficiently long acquisition time. Depending on the FOV and the desired spatial resolution, the time necessary to provide the degree of sampling required to achieve this spatial resolution can range from ten seconds to several minutes. Second, the initiation of the MRI data acquisition must be matched to the arrival of the contrast-enhanced blood within the vessels of interest, and this injection-to-arrival time is variable from patient to patient. Third, it is generally desirable to generate an angiogram in which there is negligible contrast enhancement within the companion venous system. These challenges have been addressed in various ways. For example, short repetition time ("TR") gradient echo sequences allow rapid collection of MRI data. Synchronizing the acquisition to the contrast arrival can also be done using a test bolus or fluoroscopic triggering. Extension of the acquisition duration well into the venous phase, but with intrinsic suppression of venous signals, can be done using various centric phase encoding view orders.

Parallel imaging is a method whereby the redundancy in samples collected from multiple receiver coils is used to reduce the number of repetitions of the pulse sequence, and thus the acquisition time, that is necessary to generate an image with a given spatial resolution. Parallel imaging is generally implemented by a modification of the sampling of k-space along one or more phase encoding directions. These phase encoding directions are commonly the $k_y$ direction for two-dimensional acquisitions, and both the $k_y$ and $k_z$ directions for three-dimensional acquisitions. Although parallel imaging can be implemented in non-Cartesian MR acquisitions, most applications to date have used Cartesian approaches with 2DFT or 3DFT sampling.

The degree of undersampling provided by a parallel acquisition is referred to as the acceleration, R. For a 3DFT acquisition, the undersampling can be applied separately along both the $k_y$ direction, providing an acceleration $R_y$, and along the $k_z$ direction, providing an acceleration $R_z$. Undersampling in two directions like this results in an overall acceleration of $R=R_y \times R_z$. The reduction in acquisition time achievable with parallel imaging acquisitions has allowed time-resolved methods to be used with frame times in the 5-10 second range, and with spatial resolution superior to that of non-accelerated acquisitions.

Implementation of parallel acquisition requires extra data and extra mathematical processing beyond that of standard image reconstruction. The extra data includes images of the sensitivity profiles of the individual receiver coils over the object. For image-space-based approaches to parallel acquisition, such as SENSE, the coil sensitivity maps are generated from separate acquisitions, generally made before the SENSE-accelerated scan. For k-space-based approaches to parallel acquisition, such as GRAPPA, the additional data is acquired within the accelerated acquisition, increasing the overall number of points acquired and forcing the acceleration, R, to be reduced to some smaller value, $R_{net}$. The key point of this discussion is that for both approaches to parallel imaging, there is overhead time required for the implementation of the parallel acquisition, primarily due to the need to acquire calibration data.

For example, referring to FIG. 1, a schematic timing diagram for a SENSE-accelerated, contrast-enhanced MR angiographic (CE-MRA) imaging examination 10 illustrates traditional practices. As illustrated, the examination 10 is divided into several phases of examination. First, a calibration scan phase 12 is performed in which calibration data is acquired that provides sensitivity profiles of the individual coils used in the RF imaging coil. The duration of this is typically 20 to 40 seconds long.

This is followed by a variable-length delay period 14 in which patient positioning is recorded and reconfirmed and the pulse sequence used for during the calibration scan phase 12 is swapped out for that used for the actual contrast-enhanced image acquisition. That is, the pulse sequence used for calibration is generally different from that used for the contrast-enhanced image acquisition, at least in that the repetition time (TR) can be longer and the flip angle smaller. In any case, this delay period 14 may be several tens of seconds long.

Next, the bolus of contrast agent is injected into the imaging subject at the injection phase 16. Thereafter, a pre-contrast enhancement period 18 occurs while the injected contrast agent flows through the right heart, pulmonary vasculature, and left heart, and eventually reaches the targeted arterial vasculature. This "pre-contrast" enhancement phase 18, from the injection phase 16 to arrival of the contrast agent in the arteries 22 of the vessels of interest, may be 10 to 30 seconds or longer, depending on the targeted vascular region and the patient's physiology. When the contrast agent reaches the targeted arterial vasculature, the imaging acquisition phase 20 can begin, but is preferably timed to a period of substantial contrast enhancement 22 and is completed before the contrast agent passes throughout the body, for example, through the venous structures, and the contrast-enhancement curve reflects dispersion 24 of the contrast agent.

As stated above, the duration of the combined calibration phase 12 and delay phases 14 alone can typically be 30 to 60 seconds long. Although this may not, in the abstract, seem like a long duration, it can be highly problematic for imaging of the thoracic, abdominal, or pelvic vasculature. Also, it is critical in SENSE-based parallel imaging acquisitions that the position of the object be the same for both the calibration and the accelerated imaging phases. If this is not the case, then the mismatch between object positions can cause ghost-like artifacts which can interfere with interpretation of the contrast-enhanced images. Thus, this duration can be even further extended, which undermines the speed and efficiency sought to be gained by the use of parallel imaging.

It would therefore be desirable to provide a method for parallel imaging in which calibration data could be acquired without a reduction in acceleration, R, without additional constraints on data acquisition time, and without requiring careful measures to ensure proper alignment of the patient's position between acquisition of the calibration data and the parallel, contrast-enhanced image acquisition.

SUMMARY OF THE INVENTION

The present invention overcomes the aforementioned drawbacks by providing a method for parallel imaging in which calibration data is acquired during the time period when the contrast agent is in transit from the injection site to the targeted arterial vasculature. By doing so, the preparation and examination process can be greatly streamlined and the delays associated with pulse sequence downloads eliminated. Furthermore, image quality, for example, in abdominal magnetic resonance angiography studies, can be improved by allowing all data acquisition to be done within a single breathhold. Thus, the present invention improves the temporal scan requirements of parallel imaging acquisitions.

In accordance with one aspect of the invention, a magnetic resonance imaging (MRI) system is disclosed that includes a magnet system configured to generate a polarizing magnetic field about at least a portion of a subject arranged in the MRI system and a magnetic gradient system including a plurality of magnetic gradient coils configured to apply at least one magnetic gradient field to the polarizing magnetic field. The MRI system also includes a radio frequency (RF) system configured to apply an RF field to the subject and to receive magnetic resonance signals therefrom in parallel. The MRI system further includes a computer system programmed to control operation of the magnetic gradient system and RF system to perform a calibration data pulse sequence to begin acquiring calibration data for use in a parallel imaging reconstruction process after receiving an indication that the subject has received a dose of a contrast agent. The computer system is further programmed to discontinue acquisition of the calibration data before the contrast agent reaches a peak concentration within a region of interest (ROI) of the subject, control operation of the magnetic gradient system and RF system to perform an imaging pulse sequence in accordance with a parallel imaging acquisition to begin acquiring image data from the ROI, and reconstruct the image data into an image of the ROI using the calibration data.

In accordance with another aspect of the invention, a method for producing contrast-enhanced angiographic images of a subject with a magnetic resonance imaging (MRI) system is disclosed. The method includes, following injection of a contrast agent into a subject, performing a calibration data pulse sequence to acquire calibration data for use in a parallel imaging reconstruction process. The method also includes identifying a time when the contrast agent reaches a peak concentration within a region of interest (ROI) of the subject and discontinuing acquisition of calibration data prior to the contrast agent reaching the peak concentration within the ROI of the subject. The method further includes, performing an imaging pulse sequence in accordance with a parallel imaging acquisition to acquire image data from the ROI at least including the time when the contrast agent reaches the peak concentration within the ROI of the subject and reconstructing the image data into an image of the ROI using the calibration data.

In accordance with yet another aspect of the invention, a non-transitive, computer-readable storage medium having stored thereon a set of instructions is disclosed. The instructions, when executed by a computer processor, causes the computer processor to control a magnetic resonance imaging (MRI) system to receive an indication that the subject has received a dose of a contrast agent and, after receiving the indication that the subject has received the dose of the contrast agent, perform a first pulse sequence to acquire coil sensitivity data. The computer processor is further caused to receive an indication that the contrast agent has traveled to a region of interest (ROI) within the subject and, after receiving the indication that the contrast agent has traveled to the ROI, perform an second pulse sequence in accordance with a parallel imaging acquisition to acquire image data from the ROI. The computer processor is then caused to reconstruct the image data into an image of the ROI using the coil sensitivity data.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 2:
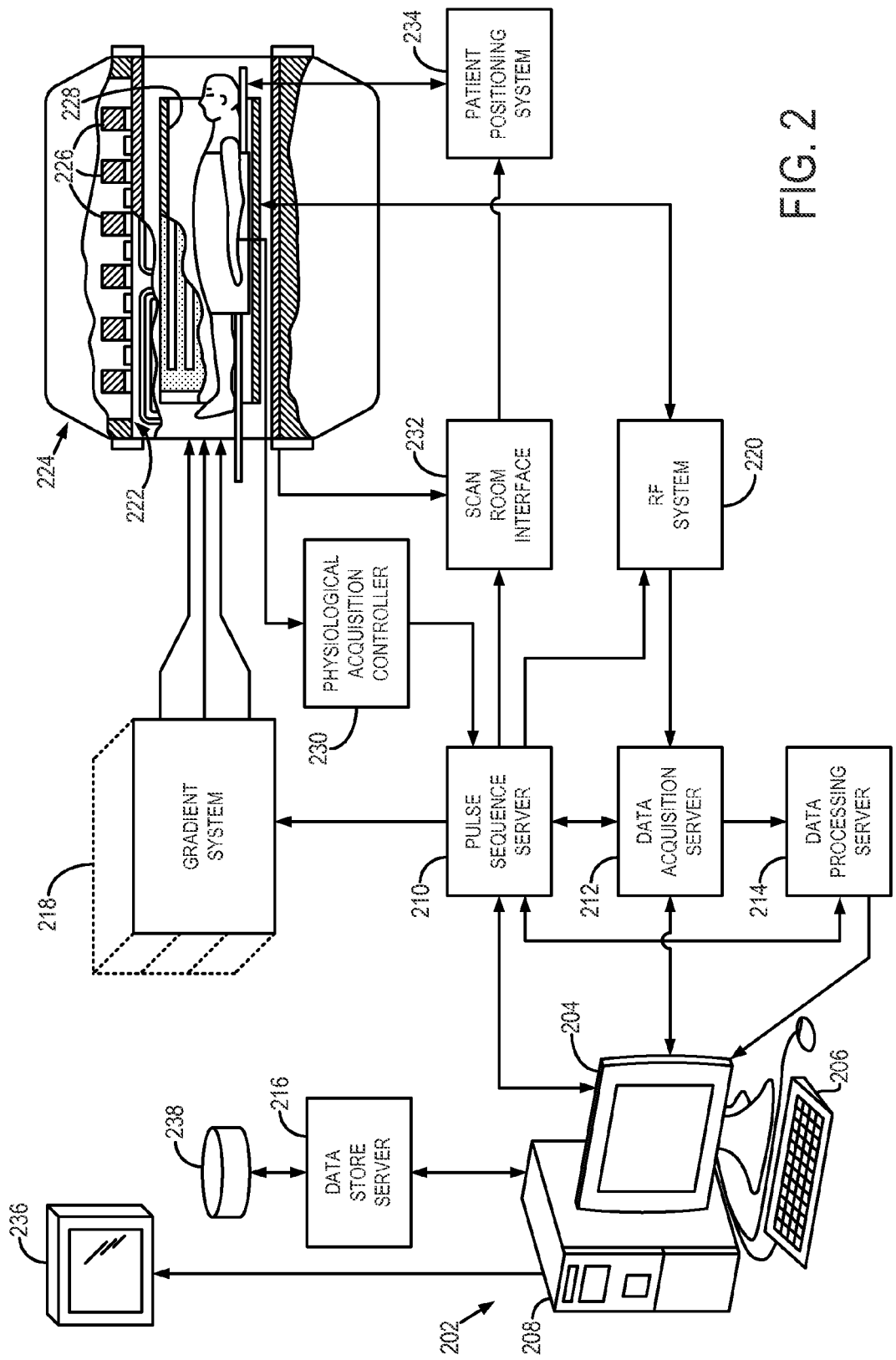
FIG. 2 is a block diagram of an example of a magnetic resonance imaging ("MRI") system for use with the present invention.

Referring particularly now to FIG. 2, an exemplary magnetic resonance imaging ("MRI") system 200 capable of practicing embodiments of the present invention is illustrated. The MRI system 200 includes a workstation 202 having a display 204 and a keyboard 206. The workstation 202 includes a processor 208, such as a commercially available programmable machine running a commercially available operating system. The workstation 202 provides the operator interface that enables scan prescriptions to be entered into the MRI system 200. The workstation 202 is coupled to four servers: a pulse sequence server 210; a data acquisition server 212; a data processing server 214, and a data store server 216. The workstation 202 and each server 210, 212, 214, and 216 are connected to communicate with each other.

The pulse sequence server 210 functions in response to instructions downloaded from the workstation 202 to operate a gradient system 218 and a radiofrequency ("RF") system 220. Gradient waveforms necessary to perform the prescribed scan are produced and applied to the gradient system 218, which excites gradient coils in an assembly 222 to produce the magnetic field gradients $G_x$, $G_y$, and $G_z$ used for position encoding MR signals. The gradient coil assembly 222 forms part of a magnet assembly 224 that includes a polarizing magnet 226 and a whole-body RF coil 228.

RF excitation waveforms are applied to the RF coil 228, or a separate local coil (not shown), by the RF system 220 to perform the prescribed magnetic resonance pulse sequence. Responsive MR signals detected by the RF coil 228, or a separate local coil (not shown), are received by the RF system 220, amplified, demodulated, filtered, and digitized under direction of commands produced by the pulse sequence server 210. The RF system 220 includes an RF transmitter for producing a wide variety of RF pulses used in MR pulse sequences. The RF transmitter is responsive to the scan prescription and direction from the pulse sequence server 210 to produce RF pulses of the desired frequency, phase, and pulse amplitude waveform. The generated RF pulses may be applied to the whole body RF coil 228 or to one or more local coils or coil arrays (not shown).

The RF system 220 also includes one or more RF receiver channels. Each RF receiver channel includes an RF amplifier that amplifies the MR signal received by the coil 228 to which it is connected, and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2};$$

and the phase of the received MR signal may also be determined:

$$\varphi = \tan^{-1}\left(\frac{Q}{I}\right).$$

The pulse sequence server 210 also optionally receives patient data from a physiological acquisition controller 230. The controller 230 receives signals from a number of different sensors connected to the patient, such as electrocardiograph ("ECG") signals from electrodes, or respiratory signals from a bellows or other respiratory monitoring device. Such signals are typically used by the pulse sequence server 210 to synchronize, or "gate," the performance of the scan with the subject's heart beat or respiration.

The pulse sequence server 210 also connects to a scan room interface circuit 232 that receives signals from various sensors associated with the condition of the patient and the magnet system. It is also through the scan room interface circuit 232 that a patient positioning system 234 receives commands to move the patient to desired positions during the scan.

The digitized MR signal samples produced by the RF system 220 are received by the data acquisition server 212. The data acquisition server 212 operates in response to instructions downloaded from the workstation 202 to receive the real-time MR data and provide buffer storage, such that no data is lost by data overrun. In some scans, the data acquisition server 212 does little more than pass the acquired MR data to the data processor server 214. However, in scans that require information derived from acquired MR data to control the further performance of the scan, the data acquisition server 212 is programmed to produce such information and convey it to the pulse sequence server 210. For example, during prescans, MR data is acquired and used to calibrate the pulse sequence performed by the pulse sequence server 210. Also, navigator signals may be acquired during a scan and used to adjust the operating parameters of the RF system 220 or the gradient system 218, or to control the view order in which k-space is sampled. The data acquisition server 212 may also be employed to process MR signals used to detect the arrival of contrast agent in a magnetic resonance angiography ("MRA") scan. In all these examples, the data acquisition server 212 acquires MR data and processes it in real-time to produce information that is used to control the scan.

The data processing server 214 receives MR data from the data acquisition server 212 and processes it in accordance with instructions downloaded from the workstation 202. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 214 are conveyed back to the workstation 202 where they are stored. Real-time images are stored in a data base memory cache (not shown), from which they may be output to operator display 212 or a display 236 that is located near the magnet assembly 224 for use by attending physicians. Batch mode images or selected real time images are stored in a host database on disc storage 238. When such images have been reconstructed and transferred to storage, the data processing server 214 notifies the data store server 216 on the workstation 202. The workstation 202 may be used by an operator to archive the images, produce films, or send the images via a network to other facilities.

Figure 3:
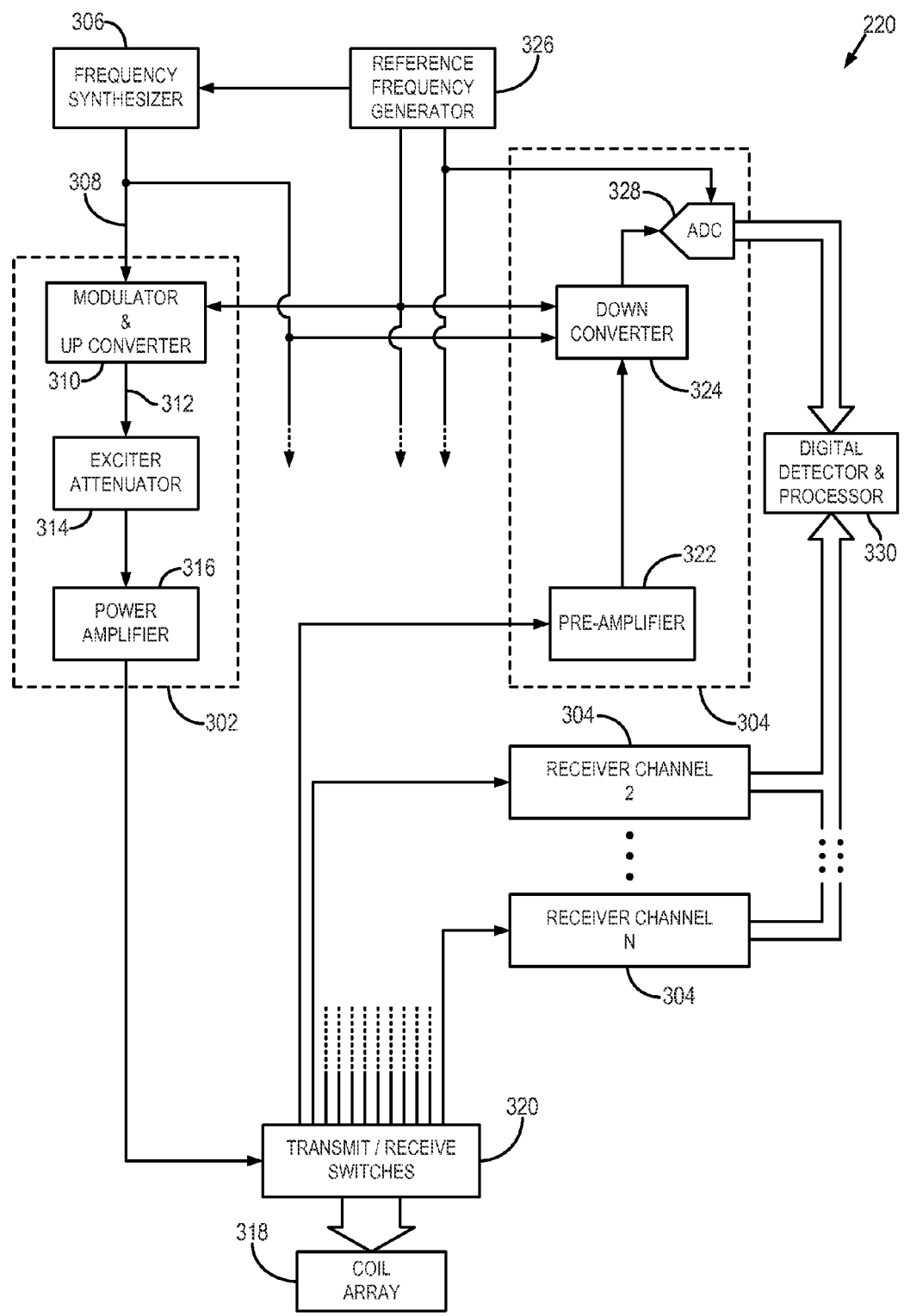
FIG. 3 is a block diagram of an example of a radio frequency ("RF") system that may form a part of the MRI system of FIG. 2.

As shown in FIG. 2, the radiofrequency ("RF") system 220 may be connected to the whole body RF coil 228, or as shown in FIG. 3, a transmitter section of the RF system 220 may connect to at least one transmit channel of a coil array 302, and its receiver section may connect to at least one receiver channel 304 of the coil array 302. Often, the transmitter section is connected to the whole body RF coil 228 or a local transmit coil (not shown), and, in so-called "parallel receiver" coil arrays, each receiver section is connected to a separate receiver channel 304.

Referring particularly to FIG. 3, the RF system 220 includes a transmitter that produces a prescribed RF excitation field. The base, or carrier, frequency of this RF excitation field is produced under control of a frequency synthesizer 306 that receives a set of digital signals from the pulse sequence server 210. These digital signals indicate the frequency and phase of the RF carrier signal produced at an output 308. The RF carrier is applied to a modulator and up converter 310 where its amplitude is modulated in response to a signal, R(t), also received from the pulse sequence server 210. The signal, R(t), defines the envelope of the RF excitation pulse to be produced and is produced by sequentially reading out a series of stored digital values. These stored digital values may be changed to enable any desired RF pulse envelope to be produced.

The magnitude of the RF excitation pulse produced at output 312 is attenuated by an exciter attenuator circuit 314 that receives a digital command from the pulse sequence server 210. The attenuated RF excitation pulses are applied to a power amplifier 316, which drives the RF coil array 318 through a transmit/receive ("T/R") switch 320.

Referring still to FIG. 3, the signal produced by the subject is picked up by the coil array 318 and applied to the inputs of a set of the receiver channels 304. A pre-amplifier 322 in each receiver channel 304 amplifies the signal by an amount determined by a digital attenuation signal received from the pulse sequence server 210. The received signal is at or around the Larmor frequency, and this high frequency signal is down-converted in a two step process by a down converter 324, which first mixes the detected signal with the carrier signal from the frequency synthesizer 306 and then mixes the resulting difference signal with a reference signal from a reference frequency generator 326. The down converted MR signal is applied to the input of an analog-to-digital ("A/D") converter 328 that samples and digitizes the analog signal and applies it to a digital detector and signal processor 330 that produces 16-bit in-phase (I) values and 16-bit quadrature (Q) values corresponding to the received signal. The resulting stream of digitized I and Q values of the received signal are output to the data acquisition server 212. The reference signal, as well as the sampling signal applied to the A/D converter 328, are produced by a reference frequency generator 326.

Figure 1:
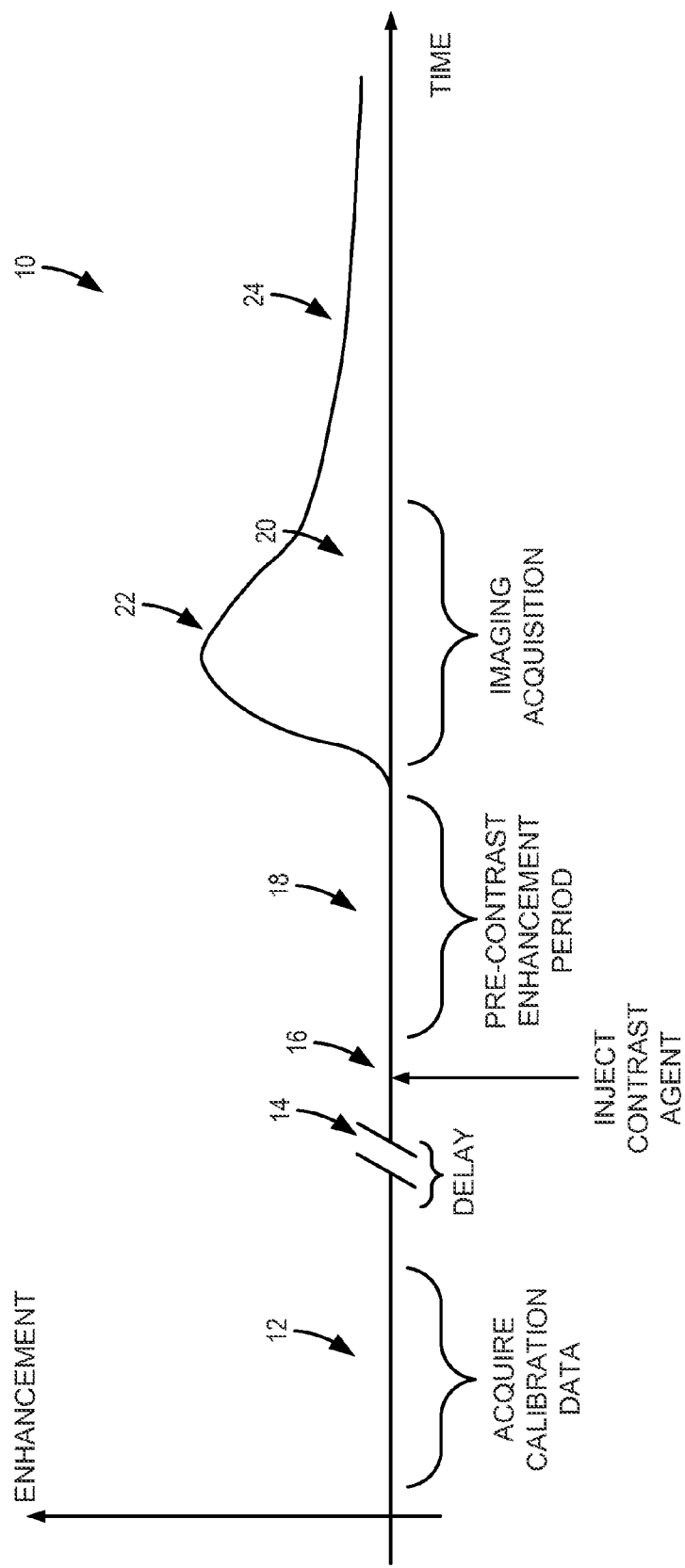
FIG. 1 is a schematic graphic representation of a process for a traditional contrast-enhanced, parallel imaging magnetic resonance (MR) angiographic study.
Figure 4:
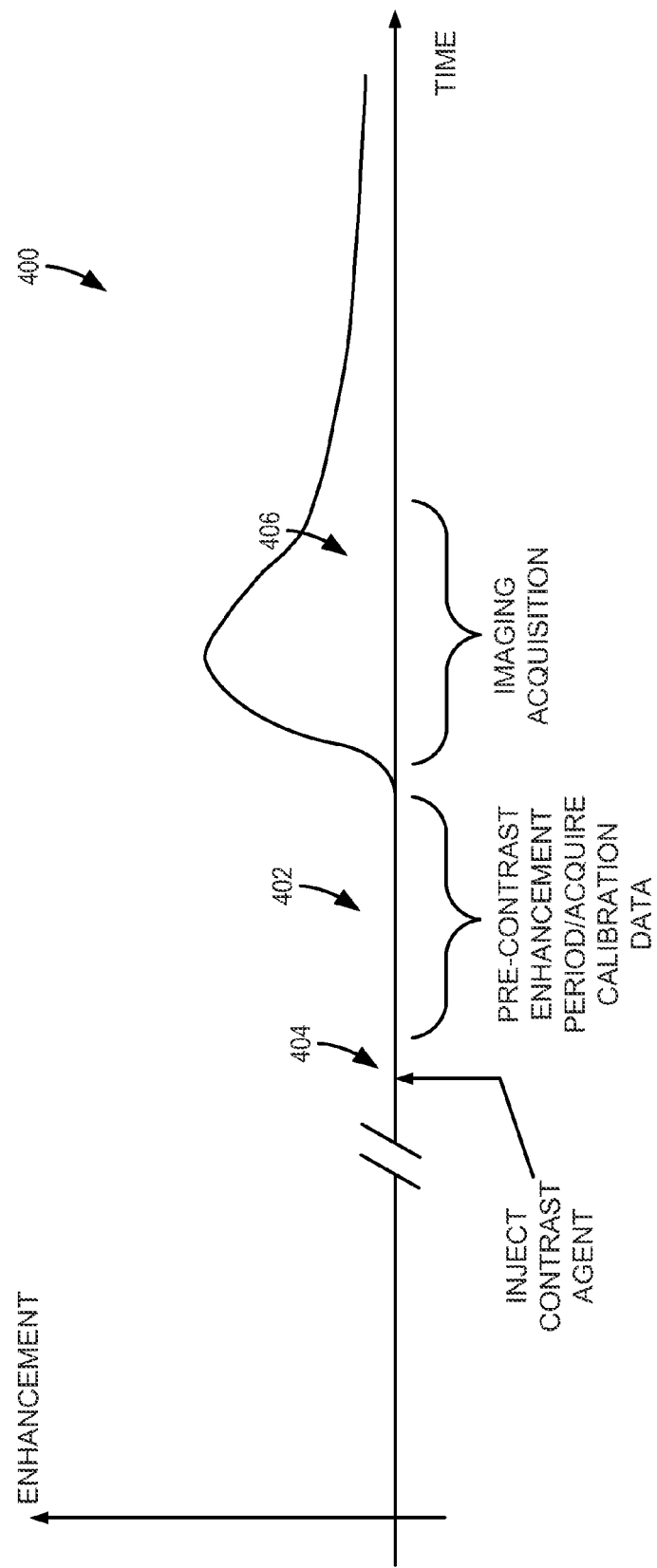
FIG. 4 is a schematic graphic representation of a process for a contrast-enhanced, parallel imaging magnetic resonance (MR) angiographic study in accordance with the present invention.

Referring now to FIG. 4, a schematic timing diagram for a SENSE-accelerated, contrast-enhanced MR angiographic (CE-MRA) imaging examination 400 in accordance with the present invention is illustrated. Unlike traditional SENSE-accelerated, CE-MRA imaging examinations as illustrated in FIG. 1 which included time dedicated to calibration data acquisition and a delay to accommodate patient positioning recording and changes between calibration pulse sequences and contrast-enhanced imaging pulse sequences, in the subject invention these times are eliminated. Instead, the pre-contrast enhancement period or "contrast transit" phase 402 that follows post contrast agent injection 404, is used for the acquisition of calibration data. As such, the process 400 begins with the injection of the contrast agent 404 and the time 402 between the injection of the contrast agent 404 and contrast enhancement phase 406 is used to acquire calibration data.

The challenge associated with acquiring the calibration data within the contrast transit phase 402 can be visualized in k-space. As is known to those skilled in the art of MRI physics, k-space is a representation of data acquisition space, which is a spatial-frequency-domain space. As described above, each point sampled during the course of the MRI data acquisition can be assigned to a location (kx, ky, kz) in k-space based upon the time varying signals of the gradient waveforms occurring up to the time instant that point is sampled. It is desirable to sample k-space across a broad range of values.

Figure 5A:
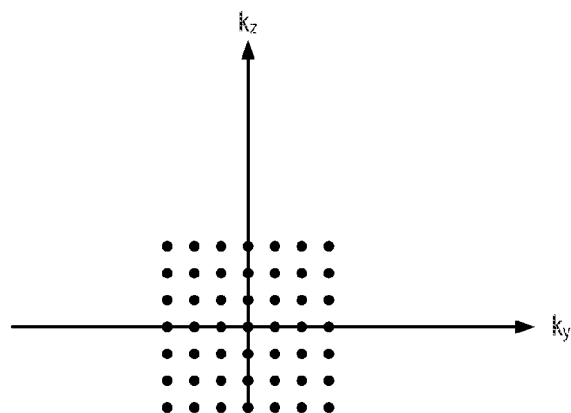
FIGS. 5A, 5B, and 5C are graphic illustrations of k-space sampling strategies in accordance with the present invention.
Figure 5B:
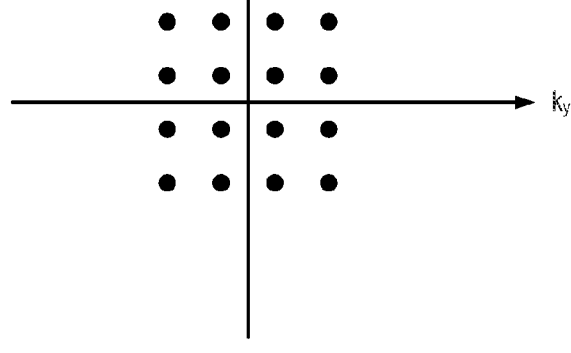
Figure 5C:
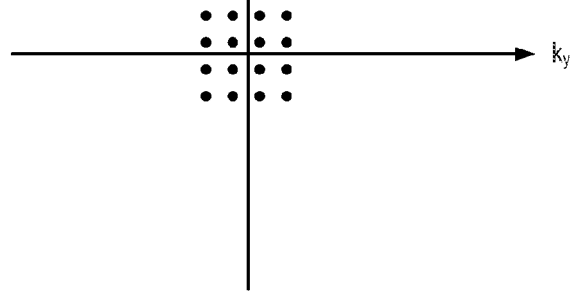

For three-dimensional (3D) Fourier transform (FT) acquisition, k-space can be represented as a grid of points arranged across a series of planes, such as illustrated in FIGS. 5A, 5B, and 5C. As convention, the kx direction is assumed to come out of the plane of the plots shown in FIGS. 5A, 5B, and 5C, and samples along the entire kx direction are generated within, for example, the short, <3 msec long echo of each repetition of the MR data acquisition. An individual sample or "view" at a specific ky-kz position of the plot is generated during each repetition of the 3DFT acquisition.

In MRI data acquisition with Cartesian sampling, the data are sampled discretely along parallel rows in ky-kz space, as shown in FIGS. 5A, 5B, and 5C. The spacing between points is equal to the reciprocal of the field of view (FOV) of the acquisition along the corresponding direction. That is, the spacing between k-space samples is given by:

$$\Delta k_y = \frac{1}{FOV_y};$$

and $$\Delta k_z = \frac{1}{FOV_z}.$$

The largest k-space value sampled along each direction is determined by how fine the spatial resolution is to be in the final image along that direction, with finer resolution causing more extended k-space sampling. Suppose, for example, that the numbers of samples along the ky and kz directions are Ny and Nz, respectively. Then, with the absence of any specific means for scan time reduction, the acquisition time $T_{ACQ}$ for a 3DFT acquisition is given by:

$$T_{ACQ} = TR \cdot N_y \cdot N_z.$$

Assuming that the sampling pattern in FIG. 5A as a standard acquisition, FIG. 5B represents an undersampled acquisition and FIG. 5C represents a calibration acquisition in accordance with the present invention.

For SENSE or SENSE-like methods, the acceleration is fundamentally obtained by sampling k-space more coarsely than in the reference scan. As an example, suppose that acceleration $R_y$ along the Y direction is set to be $R_y=2$, and similarly for Z, $R_z=2$. The resultant baseline k-space sampling pattern for this situation is shown in FIG. 5B, with the increments between samples now increased over that of FIG. 5A in proportion to the acceleration values used.

To implement an acceleration technique requires data beyond the undersampled k-space data of FIG. 5B. For a SENSE or SENSE-like method, such additional data must includes "coil sensitivity" images or maps. That is, an image of the sensitivity of each individual coil element in the receiver coil array over the object of interest must be generated. As described above, this is generally done by acquiring a calibration image, again using an MR data acquisition which can itself be analyzed in its own k-space. The sensitivity map must generally be valid over the entire FOV of the object, and consequently the sampling increment must generally be no larger than that used in the reference, where, as described above:

$$\Delta k_y = \frac{1}{FOV_y};$$

and $$\Delta k_z = \frac{1}{FOV_z}.$$

However, the present invention recognizes that, because the sensitivity map is generally smoothly varying across the object, with no abrupt changes, the spatial resolution need not be as fine as in the reference image of the object, and consequently the extent of k-space that is sampled can be reduced. A schematic k-space sampling of a calibration image that meets these conditions relative to the reference sampling of FIG. 5A is shown in FIG. 5C.

Figure 6:
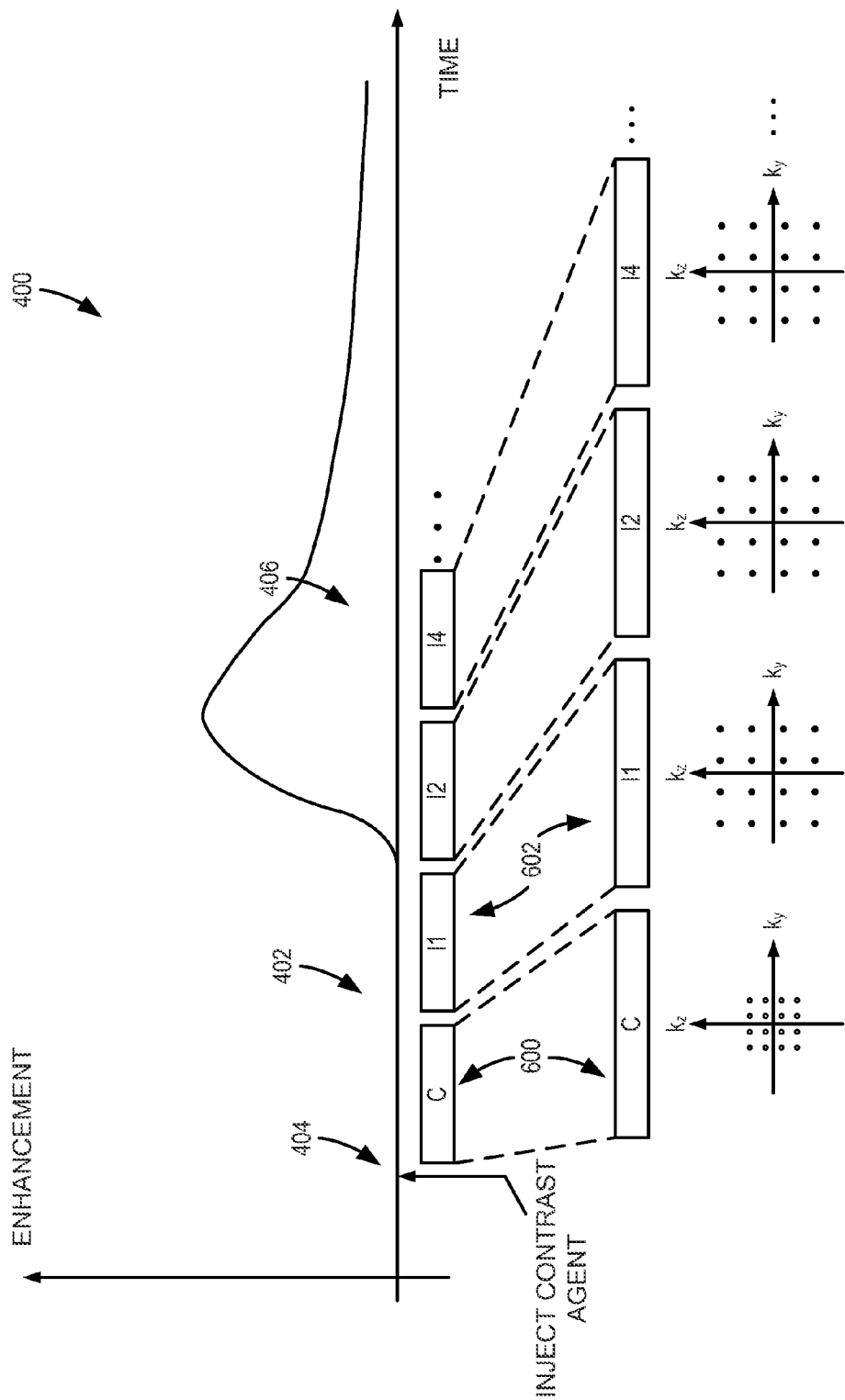
FIG. 6 is a schematic graphic representation of a process for a contrast-enhanced, parallel imaging magnetic resonance (MR) angiographic study and k-space sampling strategies in accordance with the present invention.

Referring to FIG. 6, the timing diagram of contrast dynamics and k-space sampling in accordance with the present invention are illustrated. Specifically, as described above, with respect to FIG. 4, the dedicated calibration phase and delay period are foregone and the timing diagram of contrast dynamics begins upon the injection of a contrast agent 404. Following immediately thereafter is a period pre-contrast enhancement or the "contrast transit" phase 402 that was traditionally used as a waiting period. However, in accordance with the present invention, instead of waiting or using the time between contrast injection 404 and a substantial rise in contrast in the desired vessels, calibration data 600 and even image data 602, is acquired during the contrast transit phase 402. Thereafter, subsequent image data 604, 606 is acquired that is timed to fall within the enhancement phase 406.

Even when using a common pulse sequence for the acquisition of the calibration data and the image data, so as to remove the delay created by changing pulse sequences, traditional strategies for conducting such CE-MRA studies using parallel imaging would likely lead one to conclude that there is not adequate time within the "pre-contrast" or contrast transit phase 402 of the contrast dynamics curve to acquire the calibration image with the desired spatial resolution. However, the present invention has overcome such misgivings as illustrated by the following, non-limiting example.

Suppose the FOV to be imaged is 300 (S/I)×360 (L/R)×240 (A/P) mm³. Suppose also that the desired spatial resolution of the calibration image is 4.0×4.0×4.0 mm³. Then, the number of Ny×Nz samples is (360/4)×(240/4) or 90×60=5400. If the corners of ky-kz are not sampled, then this number is reduced by 25% to 4000. Assuming a TR time of 3.0 msec, the acquisition time for the above calibration image data 600 is then 12 seconds. It is note that it may be advantageous to use further techniques to reduce acquisition times. For example, the use of homodyne reconstruction can potentially reduce the acquisition time for the calibration data by almost 50% to, in this example, about 7 seconds. This 7 second duration is generally within the pre-contrast or contrast transit phase 402 time for most anatomic regions.

The above-described system and method provides a 3D time-resolved accelerated MR image acquisition in which acquisition of calibration data is done within the pre-contrast phase of a CE-MRA process. In addition, the present invention can be readily combined with techniques, such as methods for self-calibrated parallel MR image reconstruction, such as described in co-pending U.S. patent application Ser. No. 13/478,017, which is incorporated herein by reference in its entirety Specifically, the present invention can be combined with techniques for self-calibrated parallel magnetic resonance imaging, such as described in the above-referenced, co-pending application. Both methods are applicable to time-resolved studies in which images at multiple different time frames are obtained. In the case of self-calibrated parallel magnetic resonance imaging, image data is acquired by sampling k-space in a manner sufficient to accelerate the overall acquisition while obtaining self-calibration information. By way of example, for an imaging study having thirty time frames, approximately one-thirtieth or less of the calibration data can be embedded into the acquisition time for each frame. When applied to GRAPPA-like data acquisitions, such methods advantageously reduce the amount of calibration data collected within each time frame by apportioning the data across multiple time frames. As a result, the erosion of acceleration intrinsic to GRAPPA may be reduced.

As described above, the typical sequence of scans required to generate a time-resolved series of SENSE-accelerated 3D images starts off with acquisition of the sensitivity maps using a calibration scan prior to contrast agent injection followed, much later, by a time-resolved SENSE-accelerated scan performed at, for example, times $T_1, T_2, \ldots, T_n$.

Figure 7:
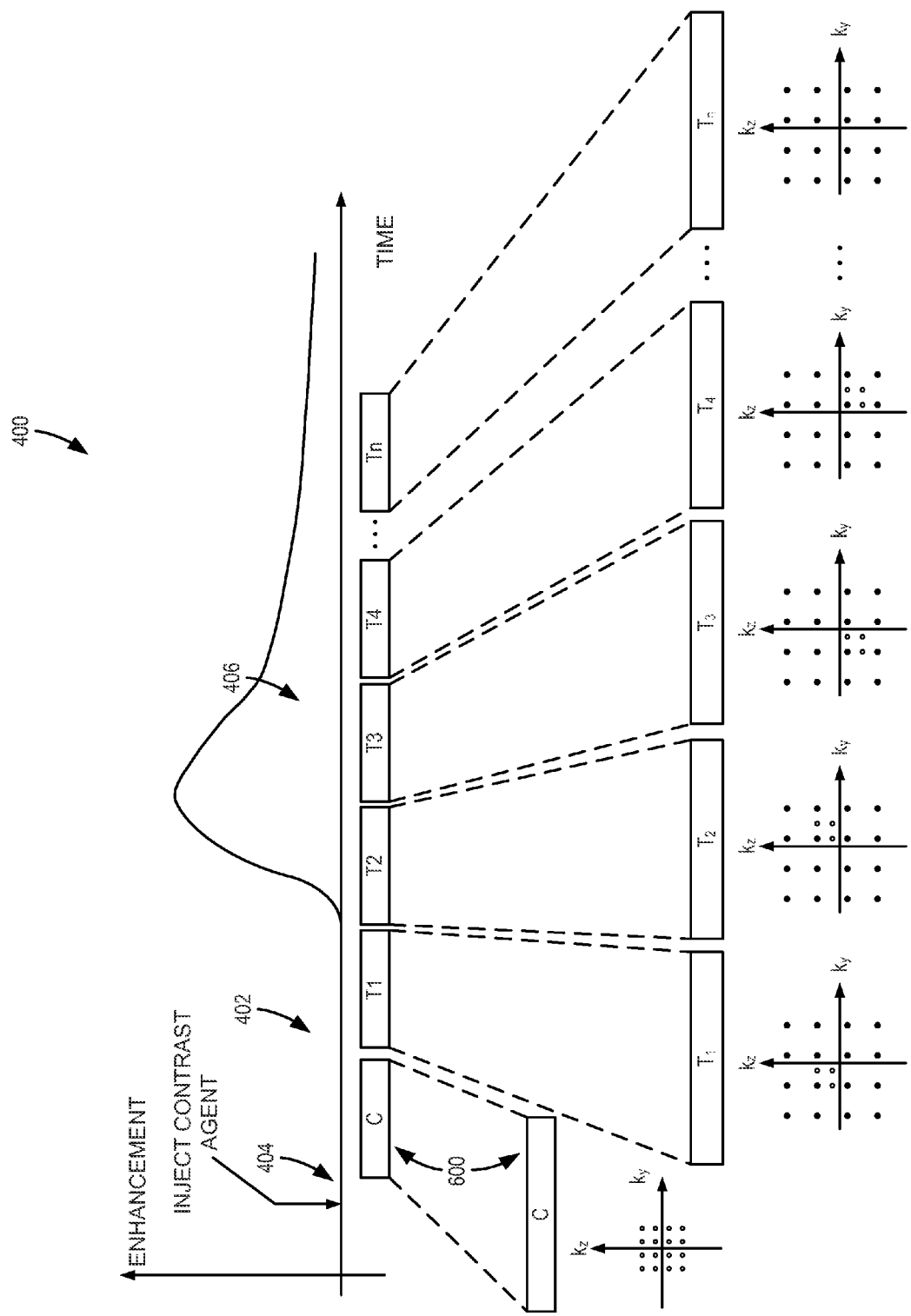
FIG. 7 is another schematic graphic representation of a process for a contrast-enhanced, parallel imaging magnetic resonance (MR) angiographic study and k-space sampling strategies in accordance with the present invention.

Specifically, referring to FIG. 7, the present invention can combined with self-calibrated parallel imaging techniques. In the case of SENSE-like accelerations, unlike traditional SENSE imaging methods, as described above, the separate calibration scan is eliminated and the calibration data acquired 600, at least partially, just after contrast agent injection 404. However, in addition to the above-described techniques, some or additional calibration data acquisitions can be integrated into the overall data acquisition process. For example, as illustrated in FIG. 7, a first time frame acquired at time $T_1$ includes image data samples at a plurality of k-space locations indicated by the black points. In addition to these image data samples, a number of calibration data samples are acquired by sampling the k-space locations indicated by the white circled points. While this acquisition scheme increases the time required to acquire any given time frame, the provided method has the benefit of eliminating the otherwise time-consuming calibration step.

One might expect that the total time spent in calibration and the multiple SENSE acquisitions does not change. That is, one might expect that the elimination of the separate calibration scan is balanced by the addition of acquiring calibration data during the data acquisition process; however, it has been discovered that overall scan time can be reduced by implementing the provided method. This is occurs whenever a given k-space location is to be sampled both for calibration and for SENSE acceleration. For example, as illustrated in FIG. 7, the additional calibration data and image data can be overlapped at some locations in k-space, thereby eliminating the need to redundantly sample the same k-space location as would be the case with a separate calibration scan. Thus, a marked decrease in scan time can be achieved with the provided method as compared to those data acquisition methods that require a separate calibration scan.

Application of the provided method to GRAPPA using, for example, the sampling scheme illustrated in FIG. 7 is also possible because the calibration data is integrated with the overall acquisition. In this example, only nineteen locations are sampled per time frame, which is only about thirty percent of the Nyquist criterion. Thus, the erosion of the nominal acceleration of R=4 is mitigated and the net acceleration factor, $R_{net}$, is 3.36, which is not nearly as severe as 2.28 in the previous example.

The above implementations of time-resolved SENSE and GRAPPA have assumed that the entirety of the undersampled k-space is sampled each time frame. It is also possible, however, to combine the provided method with sampling patterns in which view sharing is performed. In such methods, certain image data samples will be shared from one time frame to the next, thereby providing a further decrease in scan time without detrimentally affecting net acceleration.

Figure 8:
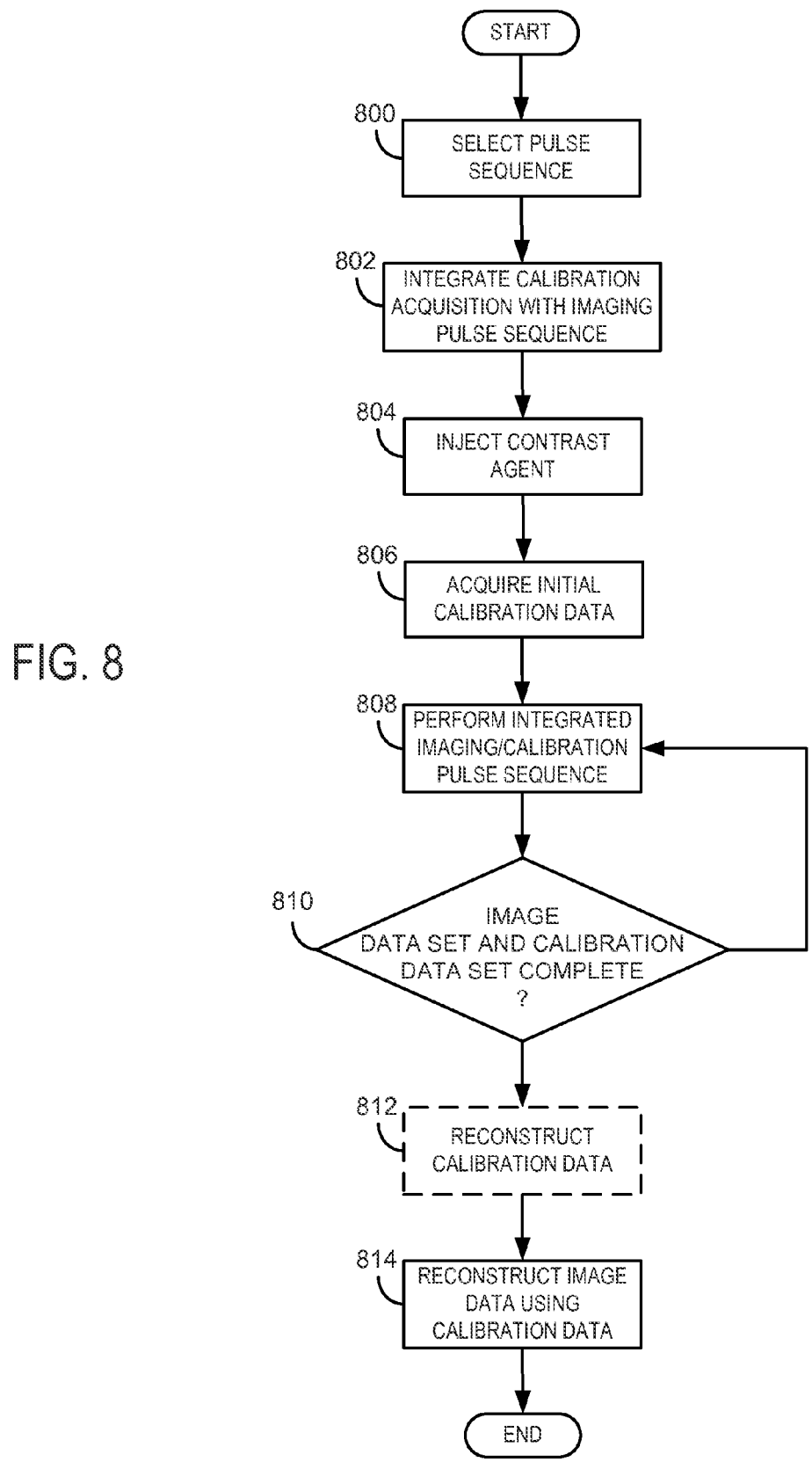
FIG. 8 is a flow chart setting forth the steps of an exemplary process for medical imaging in accordance with the present invention.

Referring now to FIG. 8, a flow chart is illustrated that sets forth general steps of a method in accordance with the present invention that can be implemented using systems such as described above with respect to FIGS. 6 and 7. Specifically, at process block 800, the clinician selects a desired pulse sequence and associated parallel imaging technique. For example, any of a variety of pulse sequences may be selected, as well as parallel imaging techniques, including SENSE and GRAPPA parallel imaging techniques.

At process block 802, the selected pulse sequence is integrated with the pulse sequence to be used to acquire the calibration data, such as described above. That is, as described above, the calibration data and image data can be overlapped at some locations in k-space during acquisition of the image data. By doing so, the need to redundantly sample the same k-space location, as would be the case with a separate calibration scan, can be eliminated. Thus, a marked decrease in scan time is achieved by combining the collection of image data and calibration data. It is also possible, however, to combine the provided method with sampling patterns in which view sharing is performed. In such methods, certain image data samples will be shared from one time frame to the next, thereby providing a further decrease in scan time without detrimentally affecting net acceleration.

At process block 804, the contrast agent is injected into the subject. Thereafter, during the contrast agent transit period, initial calibration data is acquired, such as indicated by process block 806. As explained above, conventional thinking might lead one to believe that there is not adequate time within the "pre-contrast" or contrast transit phase of the contrast dynamics curve to acquire all of the calibration data with the desired spatial resolution. In such cases, additional reductions in the time required to acquire the calibration data may be achieved using, for example, homodyne processing or other processes for reducing the duration of the calibration data acquisition. Additionally or alternatively, however, only part of the calibration data may be acquired immediately following injection of the contrast agent at process bock 804 and during the contrast transit phase and additional calibration data may be acquired thereafter using methodologies described above with respect to FIG. 7.

Specifically, additional calibration data may be acquired using the integrated imaging/calibration pulse sequence at process block 808. In accordance with some aspect of the present invention, a time-series undersampled k-space data set is acquired. The time-series undersampled k-space data set includes a selected number of k-space data subsets that include both image data and calibration data. Such data subsets that include both image data and calibration data can be referred to as "combined data sets." Within the selected number of k-space data subsets or combined data sets, the calibration data includes a portion of a desired total amount of calibration data. Furthermore, the calibration data and image data can be overlapped at some locations in k-space. Of course, not all of the image data will be or need be contained within such data subsets or so-called combined data sets.

The provided method of apportioning the acquisition of the calibration data across multiple time frames can be applied to the GRAPPA acceleration technique and to the SENSE acceleration technique. When applied to GRAPPA, the provided method reduces acceleration factor, R, erosion intrinsic to GRAPPA.

The pulse sequence is repeated as necessary to move through decision block 810, which yields the desired image and calibration data sets. Hence, at process block 812, the desired calibration data, which is a collection of the calibration data acquired at process block 806 and calibration data that is part of the combined data sets acquired at process block 808 may be reconstructed into calibration images. Thereafter, at process block 814, the images of the subject, for example, a time-series of images, are reconstructed using the calibration data/images. These images are substantially free of undersampling artifacts. As such, the desired images of the subject are acquired using a parallel imaging technique whereby the requisite calibration data is acquired in an integrated fashion with the image data to thereby better realize, in a practical sense, the acceleration of the parallel imaging technique.

The above described systems and methods apply to a variety of imaging techniques and extend, for example, to two-dimensional (2D) and three-dimensional (3D) imaging alike. For example, in the context of 3D imaging, a further improvement has been devised for 3D time-resolved accelerated MR image acquisitions. For SENSE-like scans, acquisition of calibration data which is normally acquired in a scan independent of the accelerated time series is embedded within the individual frames comprising the time series, thereby eliminating the requirement for a separate calibration scan prior to injection of the contrast agent. For GRAPPA-like scans, a full set of calibration data is not acquired within each time frame, but rather a fraction of the full set is acquired within each time frame, thereby reducing the penalty of diminished acceleration intrinsic to GRAPPA.

The present invention has been described in terms of one or more preferred embodiments, and it should be appreciated that many equivalents, alternatives, variations, and modifications, aside from those expressly stated, are possible and within the scope of the invention.

The invention claimed is:

1. A magnetic resonance imaging (MRI) system, comprising:
   a magnet system configured to generate a polarizing magnetic field about at least a portion of a subject arranged in the MRI system;
   a magnetic gradient system including a plurality of magnetic gradient coils configured to apply at least one magnetic gradient field to the polarizing magnetic field;

a radio frequency (RF) system configured to apply an RF field to the subject and to receive magnetic resonance signals therefrom in parallel;

a computer system programmed to:

control operation of the magnetic gradient system and RF system to perform a calibration data pulse sequence to begin acquiring calibration data for use in a parallel imaging reconstruction process after receiving an indication that the subject has received a dose of a contrast agent;

discontinue acquisition of the calibration data before the contrast agent reaches a peak concentration within a region of interest (ROI) of the subject;

control operation of the magnetic gradient system and RF system to perform an imaging pulse sequence in accordance with a parallel imaging acquisition to begin acquiring image data from the ROI; and reconstruct the image data into an image of the ROI using the calibration data.

2. The system of claim 1 wherein the computer system is further programmed to use a common pulse sequence for both the calibration data pulse sequence and the imaging pulse sequence.

3. The system of claim 1 wherein the computer system is further programmed to use a homodyne reconstruction process to reduce acquisition time for the calibration data.

4. The system of claim 1 wherein the computer system is further programmed to acquire the calibration data at a reduced spatial resolution compared to the image data.

5. The system of claim 1 wherein the computer system is further programmed to acquire the calibration data by sampling a central region of k-space more densely than a peripheral region of k-space.

6. The system of claim 1 wherein the computer system is further programmed to acquire the image data as a time-series of undersampled k-space data sets that include both an image data set and a calibration data set.

7. The system of claim 6 wherein the time-series of undersampled k-space data sets is acquired by repeatedly performing the imaging pulse sequence and wherein portions of the calibration data are acquired in a selected number of repetitions of the imaging pulse sequence in conjunction with acquiring the image data.

8. The system of claim 7 wherein the portions of the calibration data acquired in the selected number of repetitions of the imaging pulse sequence varies between each of the selected number of repetitions.

9. The system of claim 8 wherein the portions of the calibration data acquired in the selected number of repetitions of the imaging pulse sequence samples a different portion of k-space.

10. The system of claim wherein at least one sampling point in the calibration data overlaps with at least one sampling point in the image data in each repetition of the imaging pulse sequence.

11. A method for producing contrast-enhanced angiographic images of a subject with a magnetic resonance imaging (MRI) system, the steps of the method comprising:

following injection of a contrast agent into a subject, performing, with the MRI system, a calibration data pulse sequence to acquire calibration data for use in a parallel imaging reconstruction process;

identifying a time when the contrast agent reaches a peak concentration within a region of interest (ROI) of the subject;

discontinuing acquisition of calibration data prior to the contrast agent reaching the peak concentration within the ROI of the subject;

with the MRI system, performing an imaging pulse sequence in accordance with a parallel imaging acquisition to acquire image data from the ROI at least including the time when the contrast agent reaches the peak concentration within the ROI of the subject; and reconstructing the image data into an image of the ROI using the calibration data.

12. The method of claim 11 wherein the calibration data pulse sequence and the imaging pulse sequence are the same pulse sequence.

13. The method of claim 11 further comprising using a homodyne reconstruction process to reduce acquisition time for the calibration data.

14. The method of claim 11 wherein the calibration data is acquired at a reduced spatial resolution compared to the image data.

15. The method of claim 11 wherein acquiring image data includes acquiring time-series undersampled k-space data sets in which a selected number of k-space data subsets in the time-series undersampled k-space data set include both image data and calibration data, and in which the calibration data in each of the selected number of k-space data subsets includes a portion of a desired total amount of calibration data.

16. The method of claim 15 wherein the calibration data in each of the selected number of k-space data subsets includes a different portion of the desired amount of total calibration data.

17. The method of claim 16 wherein the calibration data in each of the selected number of k-space data subsets samples a different portion of k-space.

18. The method of claim 15 wherein at least one sampling point in the calibration data in each of the selected number of k-space data subsets overlaps with at least one sampling point in the image data in each of the selected number of k-space data subsets.

* * * * *